(12) United States Patent
Dalle et al.

(10) Patent No.: US 7,240,926 B2
(45) Date of Patent: Jul. 10, 2007

(54) FLUID CONNECTOR FOR MEDICAL USE AND USES THEREOF

(75) Inventors: Valéry Dalle, Gouvieux (FR); Pierrick Guyomarc'h, Ermont (FR); Jean-Luc Carrez, Ecouen (FR)

(73) Assignee: Vygon, Ecouen (FR)

( * ) Notice: Subject to any disclaimer, the term of this patent is extended or adjusted under 35 U.S.C. 154(b) by 182 days.

(21) Appl. No.: 10/517,643

(22) PCT Filed: Oct. 9, 2003

(86) PCT No.: PCT/FR03/02979

§ 371 (c)(1),
(2), (4) Date: Dec. 9, 2004

(87) PCT Pub. No.: WO2004/033023

PCT Pub. Date: Apr. 22, 2004

(65) Prior Publication Data

US 2005/0225082 A1    Oct. 13, 2005

(30) Foreign Application Priority Data

Oct. 10, 2002    (FR) .................................. 02 12581

(51) Int. Cl.
*F16L 37/00*       (2006.01)

(52) U.S. Cl. ........................ 285/308; 285/307; 604/905
(58) Field of Classification Search ................ 285/308, 285/307, 311, 321, 305; 604/905
See application file for complete search history.

(56) References Cited

U.S. PATENT DOCUMENTS

| | | | | | |
|---|---|---|---|---|---|
| 3,990,727 | A | * | 11/1976 | Gallagher | ...................... 285/26 |
| 5,213,376 | A | * | 5/1993 | Szabo | ......................... 285/39 |
| 5,466,017 | A | * | 11/1995 | Szabo et al. | ................. 285/319 |
| 5,514,117 | A | * | 5/1996 | Lynn | ............................ 604/536 |
| 5,568,946 | A | * | 10/1996 | Jackowski | ................... 285/308 |
| 5,871,471 | A | * | 2/1999 | Ryan et al. | ............. 304/167.03 |
| 5,873,610 | A | * | 2/1999 | Szabo | ......................... 285/319 |
| 6,253,804 | B1 | * | 7/2001 | Safabash | ..................... 604/416 |
| 6,280,430 | B1 | * | 8/2001 | Neftel et al. | ................. 604/411 |
| 6,688,654 | B2 | * | 2/2004 | Romero | ....................... 285/308 |
| 6,729,370 | B2 | * | 5/2004 | Norton et al. | .............. 604/411 |

* cited by examiner

*Primary Examiner*—David Bochna
(74) *Attorney, Agent, or Firm*—Levine & Mandelbaum

(57) ABSTRACT

A fluid connector, for use in the medical field, has a tubular male socket and a tubular female socket. Each socket includes a fitting end for an end piece and a nesting end. The female socket has external notches for axially retaining a locking collar which is fixed on the male socket by penetration of lugs into ports on the collar.

14 Claims, 9 Drawing Sheets

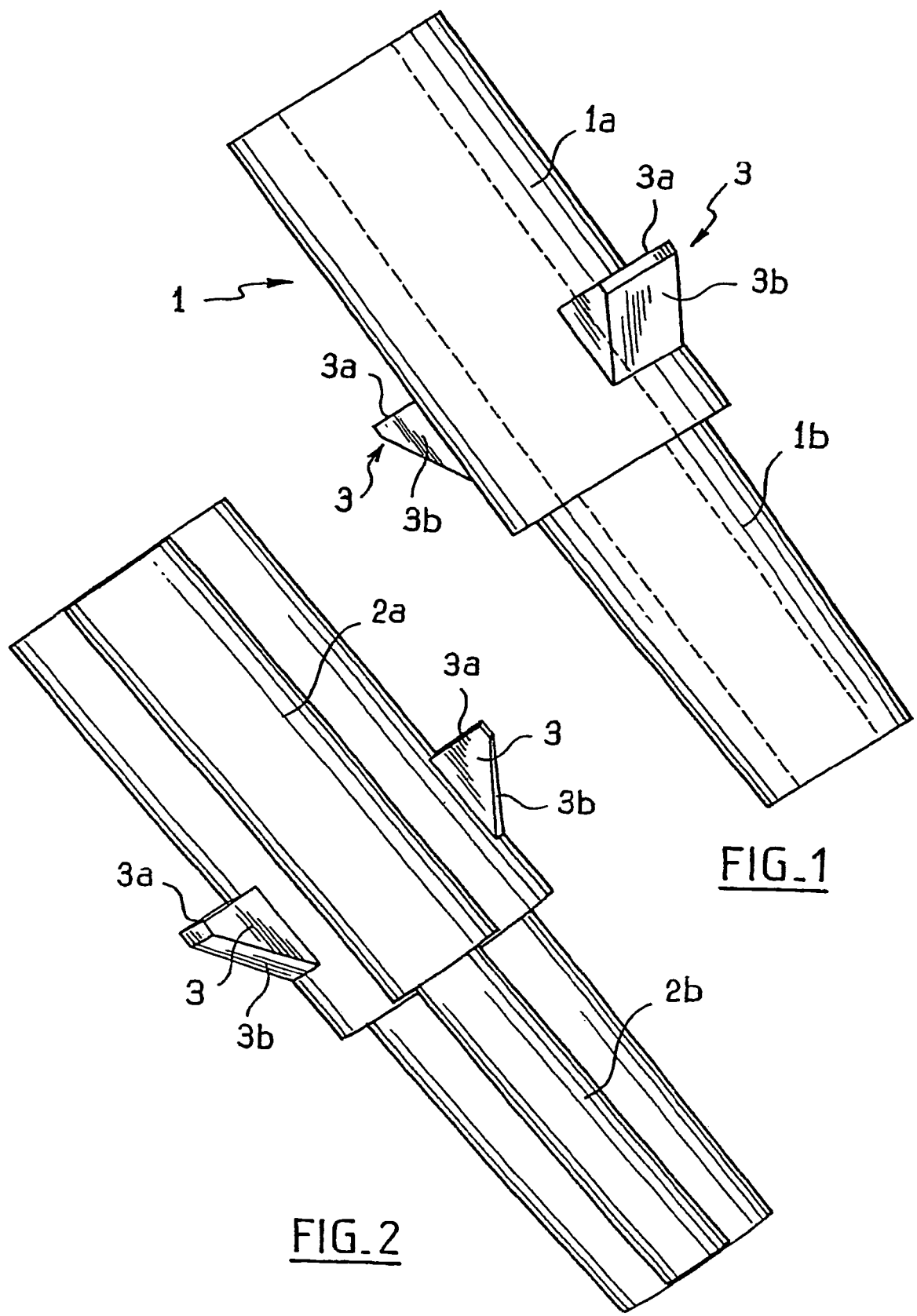

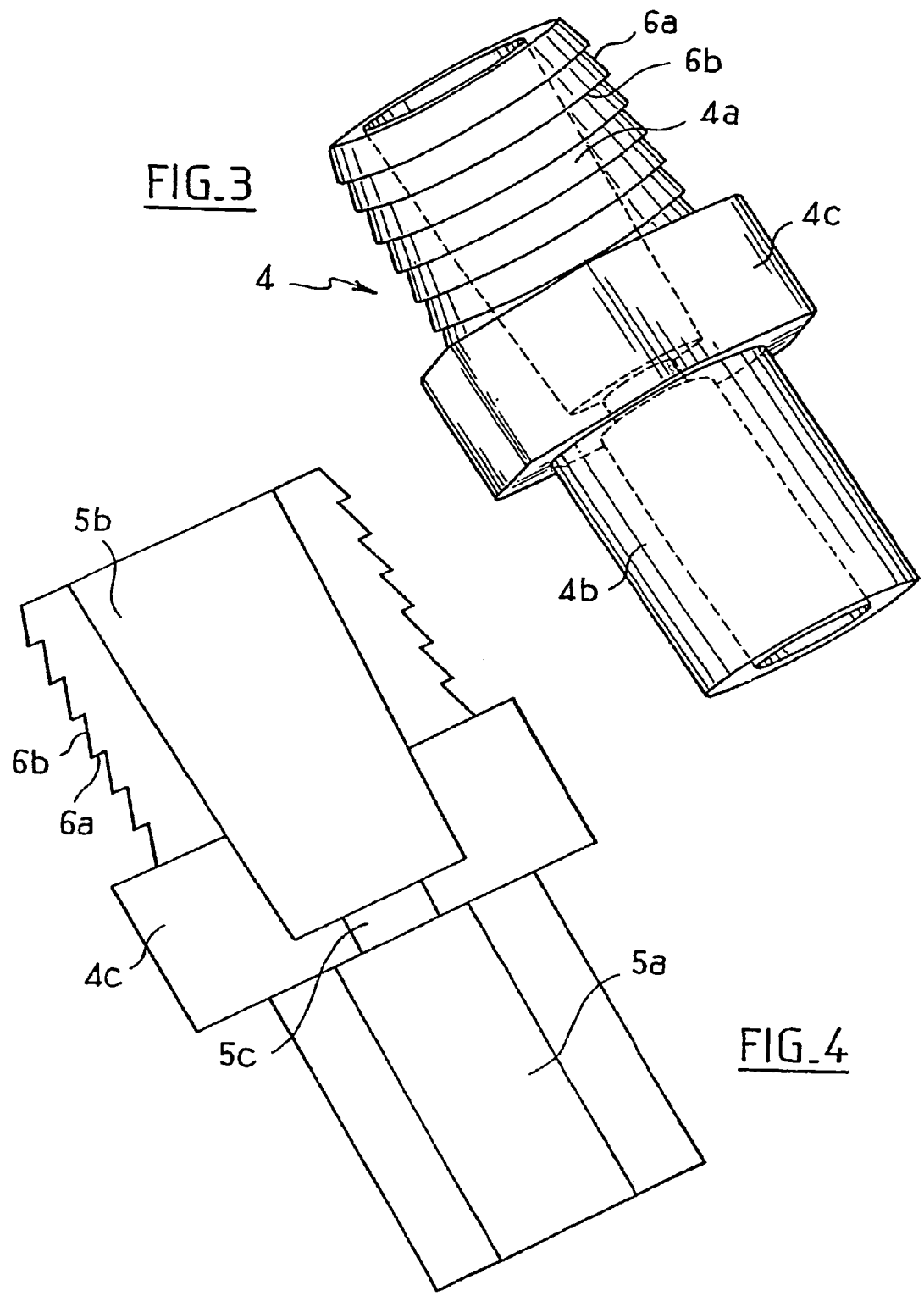

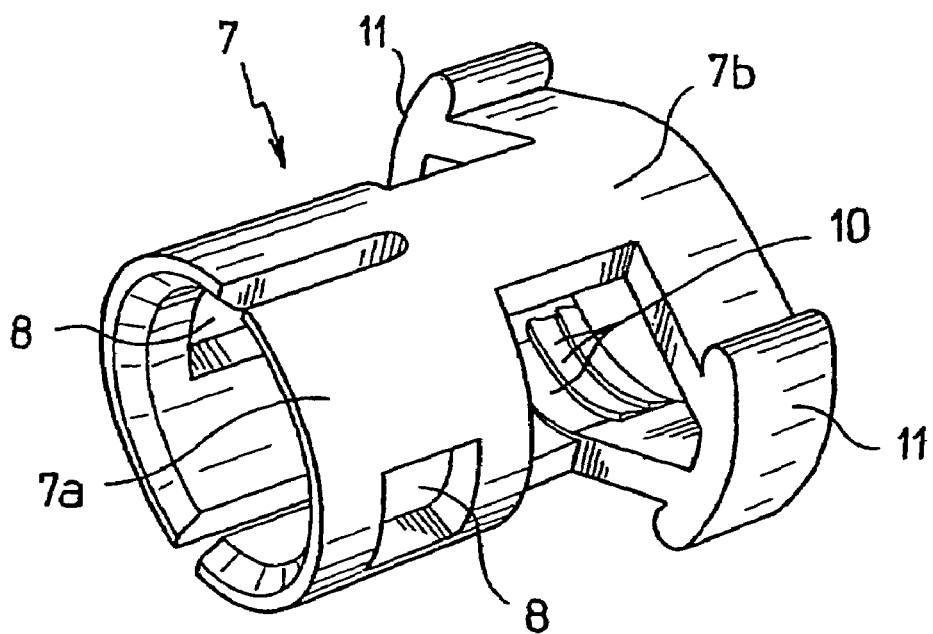
FIG_5
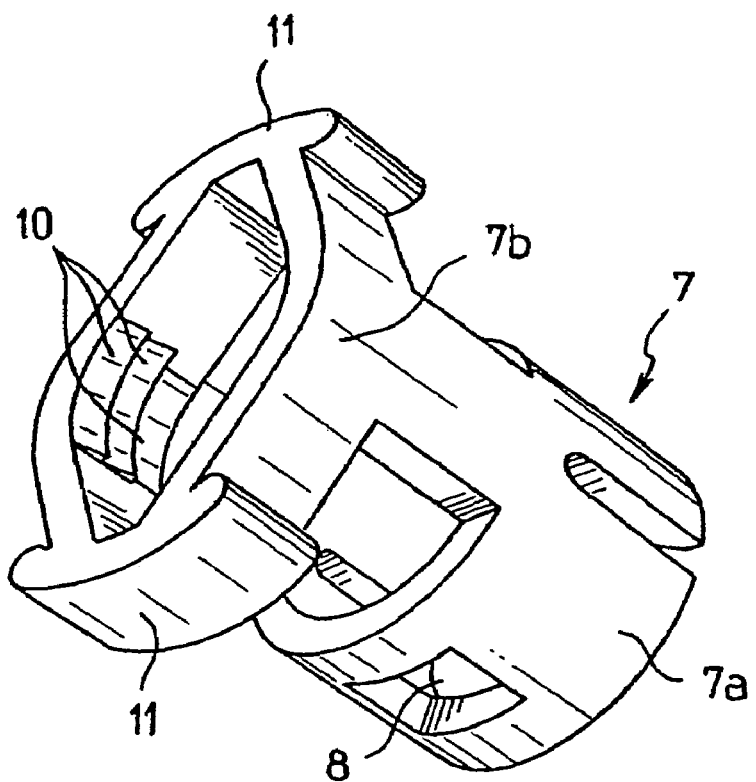
FIG_6

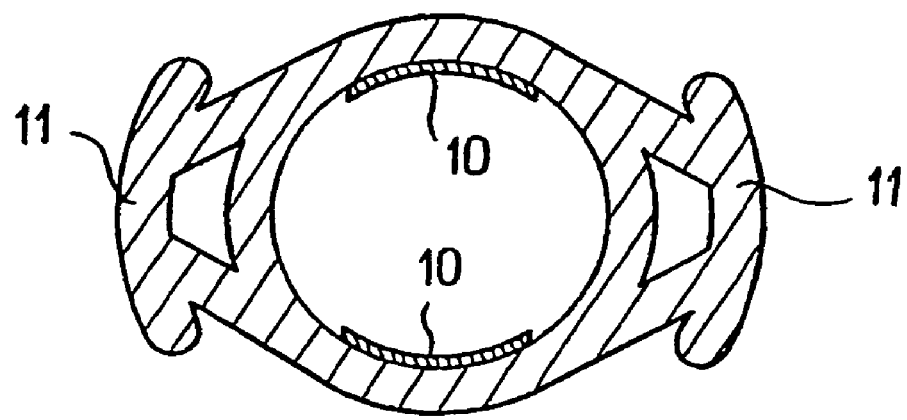
FIG_7
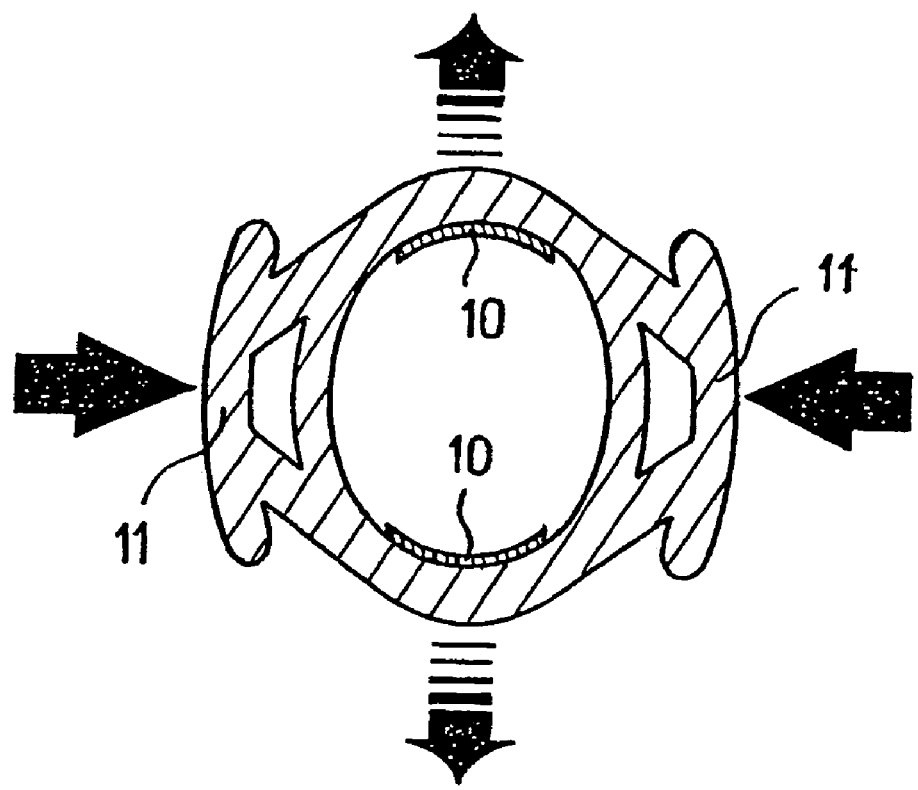
FIG_8

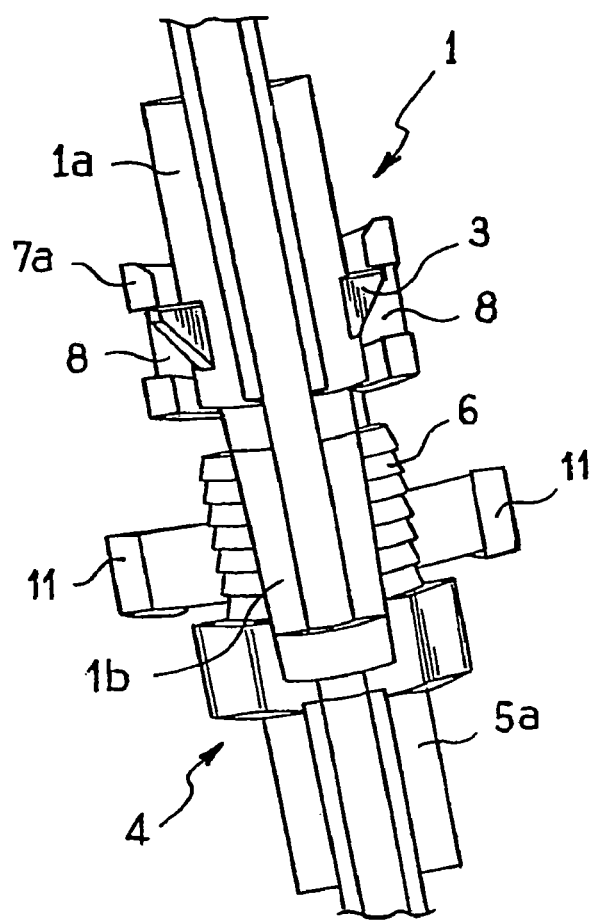
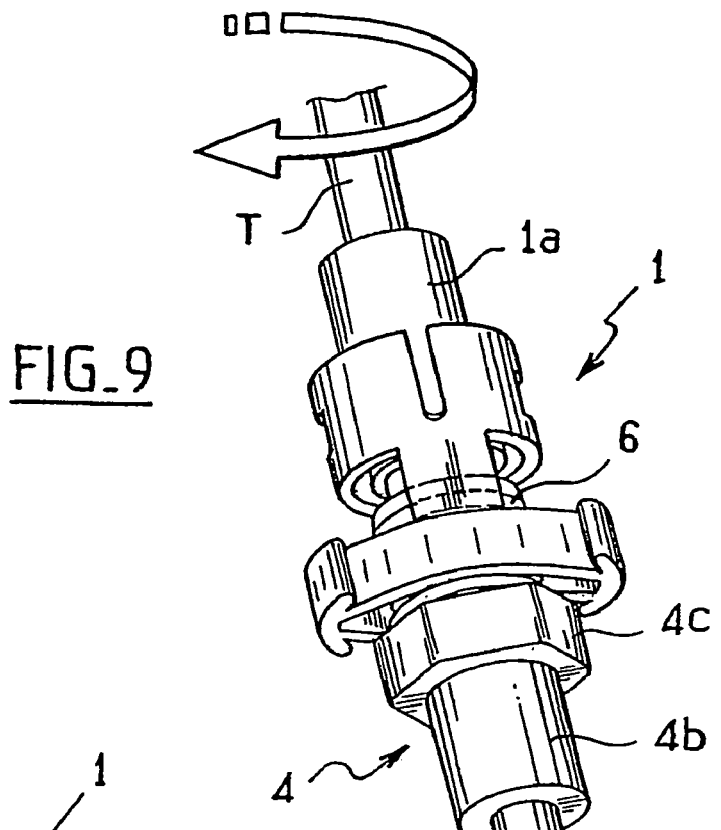
FIG_9
FIG_10

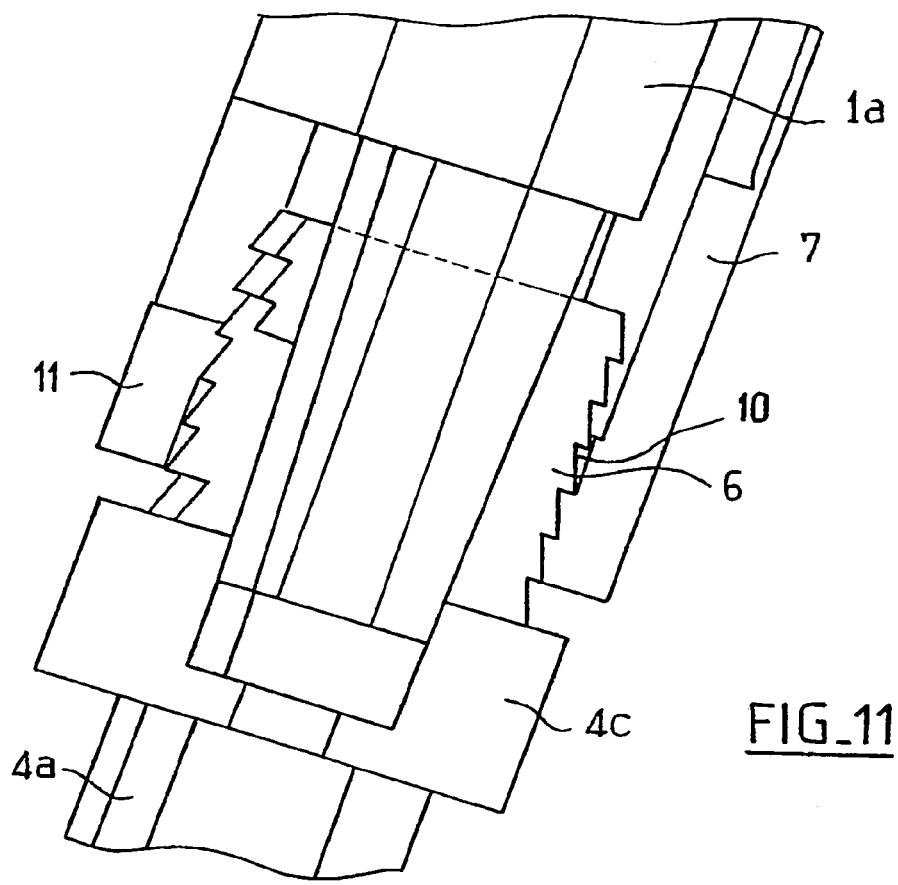
FIG_11
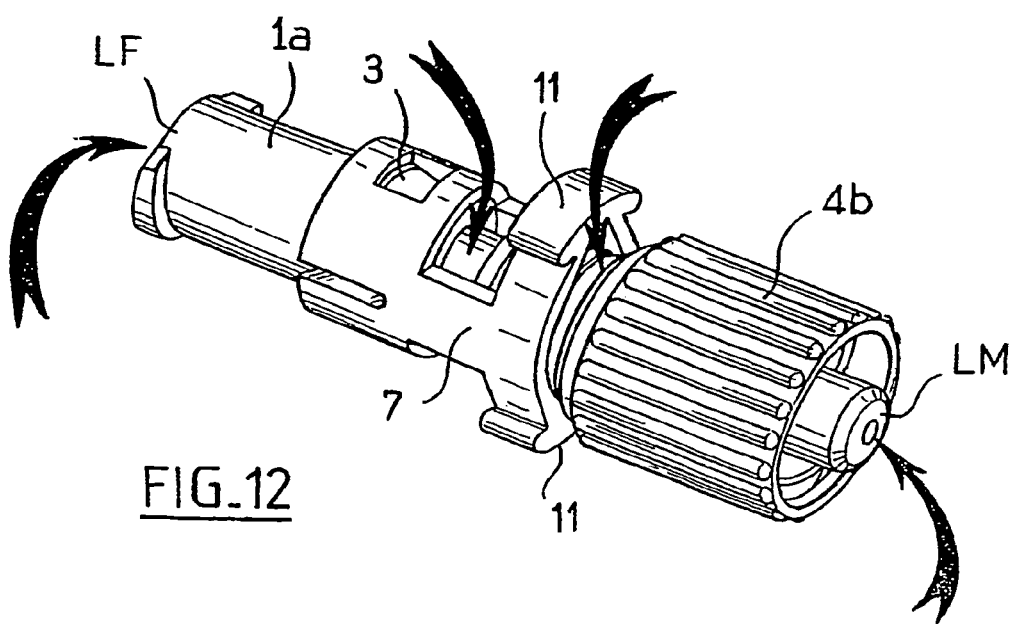
FIG_12

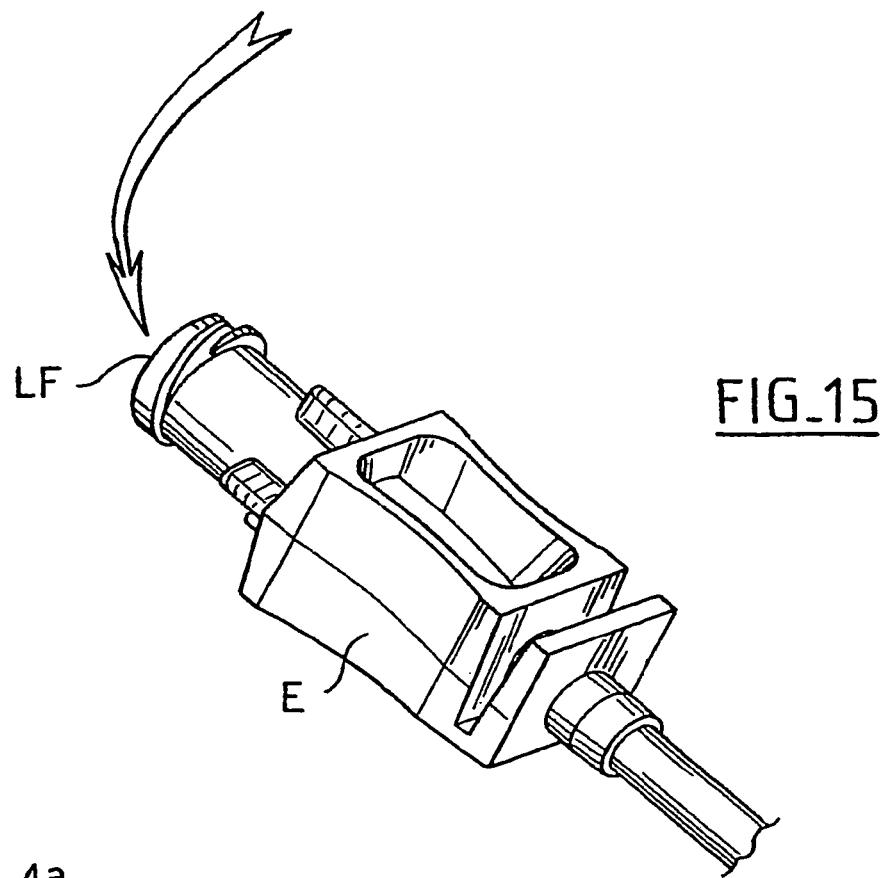
FIG_15
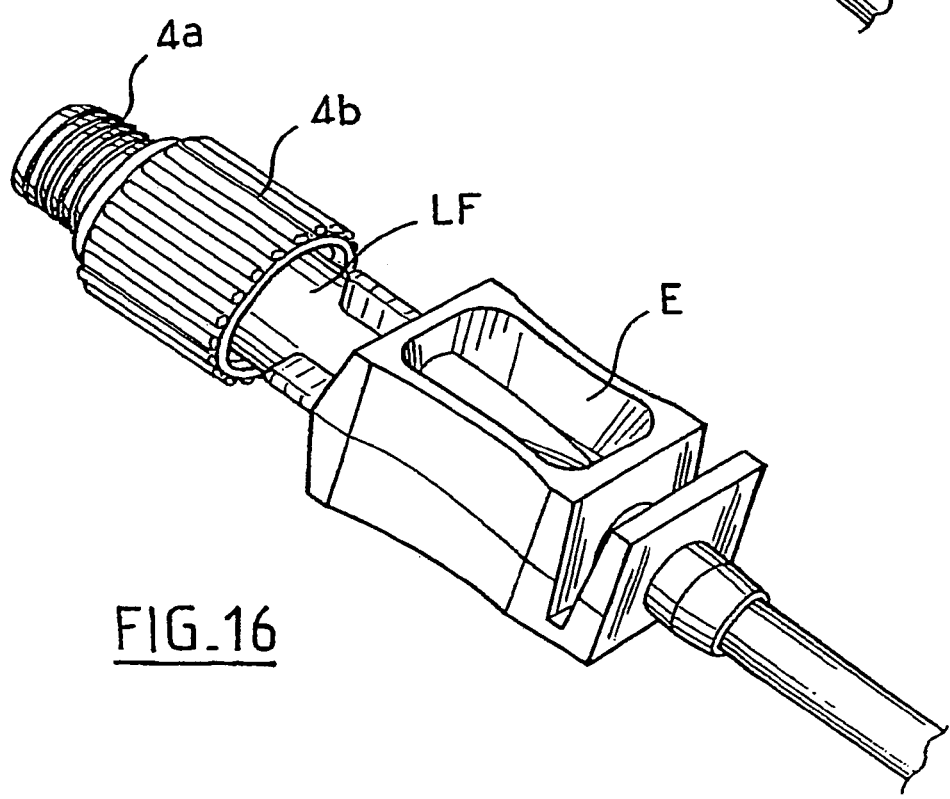
FIG_16

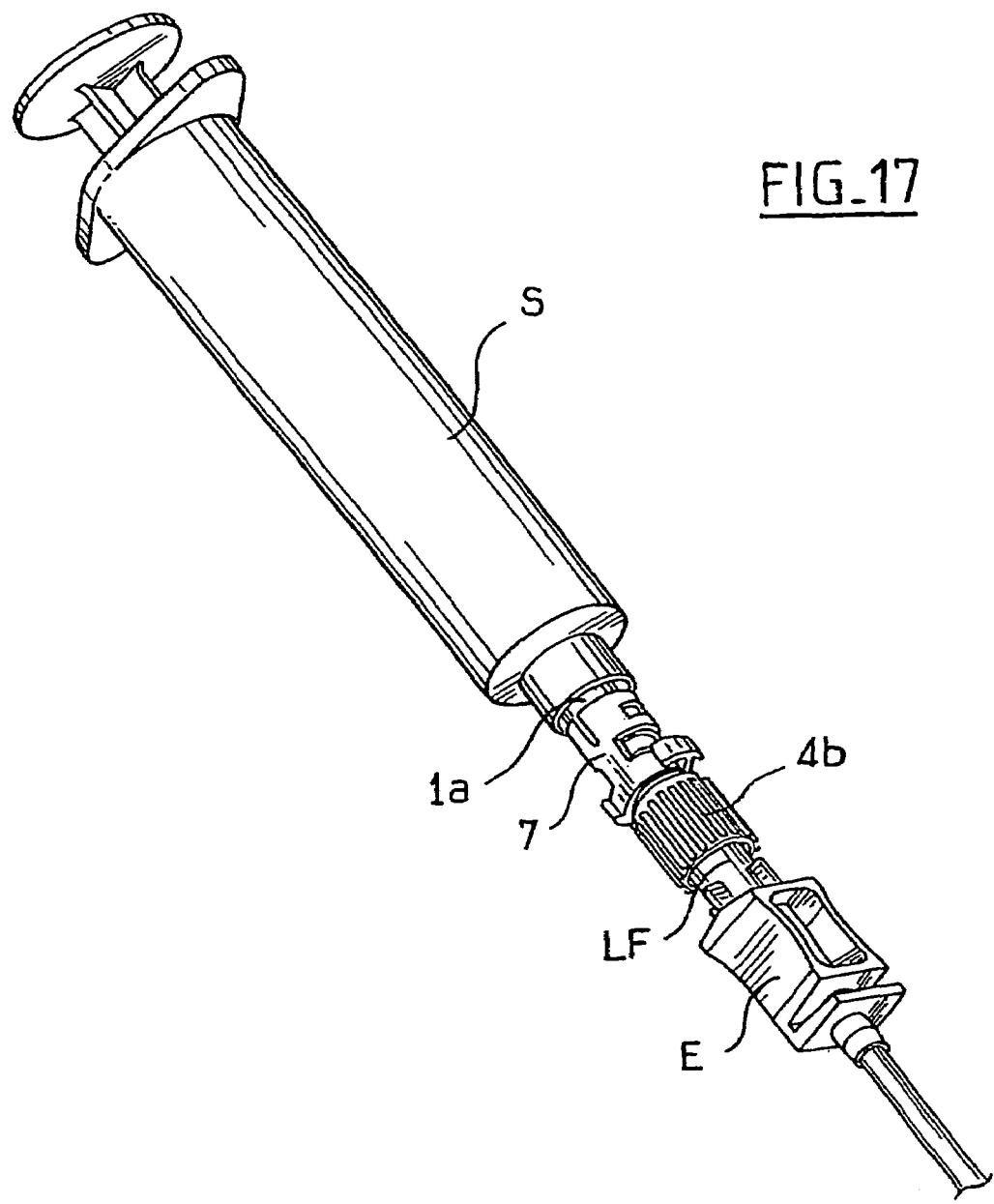
FIG_17

FLUID CONNECTOR FOR MEDICAL USE AND USES THEREOF

BACKGROUND OF THE INVENTION

The present invention relates to a connector for a fluid circuit for medical use.

It applies in particular to conical assemblies for syringes, needles and other apparatus for medical use, for example for transfusion equipment.

Generally, these assemblies use connections comprising a male socket and a female socket which fit together through conical tips (so-called Luer-type cones), with lateral seal around the fitted tips.

The security of the connection is sometimes strengthened by screwing.

In practice, two disadvantages are noted:
the connections can become unscrewed without warning due to the effect of one of the sockets being is rotated;
since the same type of connection is used for different applications, there are real risks of confusion for the nursing staff, for example setting a nutrition line into the female socket of a venous catheter.

At present, there is a need for new systems to be created in order to avoid such confusion and to make the connection more secure, so that it cannot become disconnected except through a voluntary action.

SUMMARY OF THE INVENTION

An aim of the present invention is to provide a connector able to link up with automatic locking of the connection.

Another aim of the invention is to be able to individualise the link using cones with different taper angles and different diameters depending on the applications, thus avoiding any risk of confusion because in this case, if there is an error, neither the hold nor the locking system is possible According to the invention, this aim is achieved using a connector for fluids with automatic locking constituted of a tubular male socket having a connection tip at one end-piece and a tip for fitting, of external conical shape, and of a tubular female socket having a connection tip at one end-piece and a receptor tip with internal conical shape able to receive said fitting tip of the male connector with lateral seal, the male socket being provided with external lateral lugs, the female socket being provided with a set of external notches and the connector comprising a locking collar to be mounted on the two sockets, said collar having lateral ports able to be crossed by the lugs of the male socket for blocking the collar axially and in rotation on the male socket, and said collar having a transversally deformable part and being equipped with internal notches, the notches being shaped so that the notches of the collar can pass over the notches of the female socket when the collar is pushed in a direction towards the socket and be held by the notches of the female socket when there is traction in the reverse direction, and the notches being shaped to allow relative rotation of the female socket and the collar, and the notches of the collar being able to be separated laterally from the notches of the female socket by transversal deformation of the part of the collar carrying the notches.

The word "end-piece" means any connecting tip for medical equipment.

In particular, it can concern:
the normalised Luer tip, male or female, of equipment such as a syringe S, a socket E for a needle or catheter, etc.;
the cylindrical tip of a tube T.

In the preferred embodiments, the connector furthermore has one or several of the following characteristics:
The collar comprises two series of diametrically opposite notches and two zones at 90° relative to the notches able to be pushed radially to deform the collar transversally so as to separate the two sets of notches from each other.
The notches have a slight inclination to facilitate locking by axial thrust and a steep inclination to prevent unlocking by axial traction, the locking being ensured by the contact between the steep inclinations of the collar notches and the steep inclinations of the notches of the female socket.
The notches of the female socket are grooves or portions of circular grooves.

DESCRIPTION OF THE DRAWINGS

Examples of connectors according to the invention will be described below, with reference to the attached drawings, in which:

FIG. 1 is an external view of the male socket;
FIG. 2 shows a cross-section of the male socket;
FIG. 3 is an external view of the female socket;
FIG. 4 shows a cross-section of the female socket;
FIG. 5 is a view in perspective of the locking collar;
FIG. 6 is another view in perspective of the collar;
FIGS. 7 and 8 are views in transversal cross-section of the collar, at rest and deformed respectively;
FIG. 9 is an external view of the connector in the locked state;
FIG. 10 shows a cross-section of the connector in the locked state;
FIG. 11 is an enlarged view of the locking zone of the connector in the locked state, and
FIGS. 12 to 17 show an application of a connector according to the invention, for connecting a syringe to a needle socket.

DESCRIPTION OF THE PREFERRED EMBODIMENT

Figure 13:
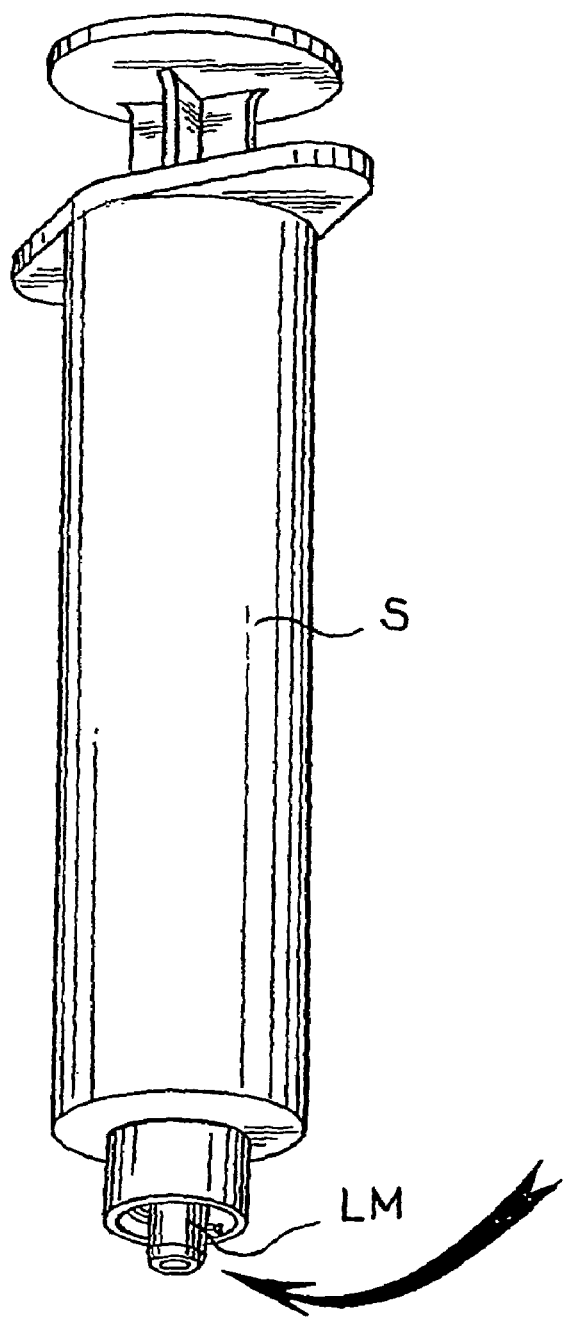

The device shown in the figures comprises (FIGS. 1 and 2) a male tubular socket 1 having an adaptable connection tip 1a and an opposite tip 1b to be fitted (FIG. 1).

The male socket is crossed by a longitudinal cylindrical channel (2) which includes a channel part 2a in the adaptor tip and a channel part 2b in the tip to be fitted. The diameter of channel 2a is greater than the diameter of channel 2b.

The adaptor tip 1a carries two lateral lugs 3 shaped like a triangle located in a same cross-section on two sides and diametrically opposite (FIG. 1). Each lug has a steep inclination 3a turned towards the adaptation tip and a gentle inclination 3b turned towards the tip to be fitted.

The tip to be fitted, 1b, is externally conical in shape.
The adaptor tip is externally cylindrical in shape.
The device shown also includes (FIGS. 3 and 4) a female tubular socket 4 comprising an adaptable connection tip 4a and an opposite tip 4b for fitting reception (FIG. 3).

The female socket is crossed by a longitudinal channel 5 which includes a channel part 5a in the adaptor tip 4a and a channel part 5b in the fitting reception tip (FIG. 4). The channel part 5a is not as wide as the channel part 5b and these two channel parts are separated by a channel part 5c, cylindrical and narrower than the two other channel parts.

The female socket has an intermediate peripheral reinforcement 4c between its tips 4a and 4b to facilitate handling.

The fitting reception tip 4b of the female socket comprises external notches 6 constituted in this example by parallel grooves having an inclined face 6a and a straight face 6b. The straight face is turned towards the adaptation tip 5a.

The adaptation tip is externally cylindrical.

The device also includes a collar 7.

The collar 7 is a tubular body which, in FIGS. 5 to 8, has a tip 7a whose lateral wall is pierced by two ports 8 able to be crossed by the lugs 3 of the male socket when the collar is slipped over this socket and pushed towards the female socket, and which has an opposite tip 7b whose lateral wall is provided, on its internal face 9, with two sets of notches 10 opposite each other able to co-operate with the notches of the female socket when the collar is pushed onto the female socket.

Furthermore, the cross-section of the collar comprising the notches 10 is widened towards the outside to form two handling zones 11 at 90° relative to the notches such that a radial thrust on these zones causes deformation of the collar thus separating the notches from each other (FIG. 8) The material of the collar is chosen so as to allow this deformation.

When the male cone is coupled in the female cone, the notches of the collar automatically pass over those of the female socket, until coupling of the two cones is complete.

Any return movement (disconnection) is rendered impossible because of the interlocking of these notches. Rotation of the male and female sockets in a reverse direction is possible without risk of disconnection.

The seal is ensured by the cone/cone contact, and the locking is ensured by the contact of the steep inclinations of the collar notches on those of the female socket notches.

Pressure on these bearing zones lifts the notches of the collar and eliminates the contact of the steep inclinations of the notches. By maintaining this effort, axial disconnection is possible.

The fact of having to make this effort to disconnect constitutes the security of this connection.

FIGS. 8 to 11 show the finished connection.

The invention makes it possible to adapt the connector to the different uses possible in the medical field without any risk of confusion, by playing on the internal diameter and the shape of the adaptation tips of the sockets.

The invention is not limited to the embodiments described.

This medical connection can function with male and female cones of different shapes, ensuring the seal, and also the impossibility of mounting and locking different shapes, the latter to avoid fixing different equipment together, for example venous access (arterial, nutritional, peridural etc.), each piece of equipment in a certain field being equipped with the correct cone (male or female).

Figure 14:
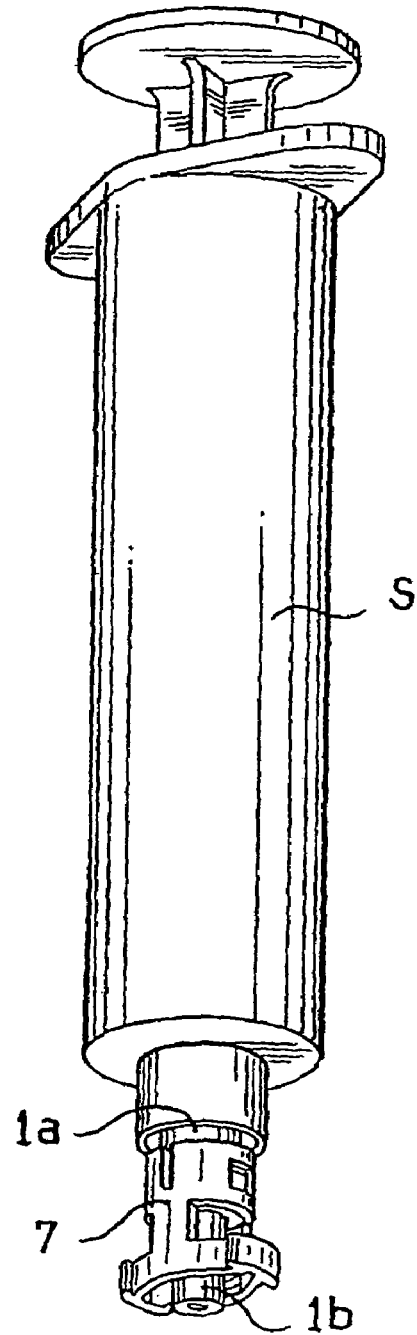

FIGS. 12 to 17 show an example of the application of a locking connector according to the invention for secured connection of a syringe S to a socket E of a needle:

FIG. 12 is a view in perspective of the connector whose male socket has its adaptation tip 1a designed internally with a female Luer cone lock LF for mounting (and gluing if necessary) on a male Luer cone of equipment to be connected, of the syringe type, the female socket of the connector having its adaptation tip 4b designed internally with a male Luer cone lock LM making it possible to be mounted (or glued if necessary) on a female Luer cone of equipment of the needle type to be connected;

FIG. 13 is a view in perspective of the syringe designed with a male Luer LM at its outlet tip;

FIG. 14 is a view in perspective of the male socket of the connector mounted on the syringe by fitting the male Luer LM of the syringe S into the adaptation tip 1a of the male socket, which is constituted internally like a female Luer LF;

FIG. 15 is a view in perspective of the socket E of the needle designed with a female Luer LF at its input tip;

FIG. 16 is a view in perspective of the female socket of the connector mounted on the socket E of the needle. For this, the adaptation tip 4b of the female socket is constituted internally like a male Luer LM able to be fitted into the female Luer LF of the socket E of the needle.

FIG. 17 is a view in perspective of the syringe connected to the socket of the needle by the connection according to the present invention.

The invention is not limited to this example of a connection.

Thus, the adaptation tip of one of the sockets of a secured connector according to the invention can be connected to a tube by internal or external interlocking, this tube serving, for example, as a link to a piece of equipment.

The invention also envisages providing a new generation of medical equipment, in particular such as needle or catheter tubes, syringes and sockets, having a connection tip constituted by one of the male and female sockets of the connector according to the invention.

Finally, the invention envisages replacing the means described by functionally equivalent means, or producing kinematic inversions, for example changing the means between one and the other connector sockets.

The invention claimed is:

1. Connector for fluids, said connector automatically locking for connecting the Luer cones of two pieces of equipment for medical use, said connector comprising a tubular male socket having an adaptation tip at one endpiece and a tip to be fitted of external conical shape, and a tubular female socket having an adaptation tip at one endpiece and a reception tip of internal conical shape able to receive said fitting tip of the male connection with a lateral seal, the male socket being provided with external lateral lugs, the female socket being provided with a set of external notches and the connector comprising a locking collar to be mounted on the two sockets, wherein said collar has lateral ports able to be crossed by said external lateral lugs of the male socket for blocking the collar axially and in rotation on the male socket, and said collar has a transversally deformable part equipped with internal notches, shaped so that the external notches of the collar can pass over the notches of the female socket when the collar is pushed in a direction towards the socket and held by the notches of the female socket when there is traction in the reverse direction, and the notches of the collar and of the female socket being shaped so as to allow relative rotation of the female socket and the collar, said collar comprising zones such that a radial thrust on these zones causes deformation of the collar thus separating the notches of the collar from the notches of the female socket in order to allow separation of the collar and the female socket.

2. Connector according to claim 1 wherein said collar comprises two sets of notches diametrically opposite each other and two zones at 90° relative to the notches able to be pushed radially to deform the collar transversally in order to separate the two series of notches from each other in order to allow separation of the collar and the female socket from the connector.

3. Connector according to claim 1 or 2 wherein the notches of the collar and the female socket have a slight inclination to facilitate and automate the locking by axial thrust and a steep slope to prevent unlocking, the locking being ensured by the contact between the steep inclinations of the notches of the collar on the steep inclinations of the notches of the female socket.

4. Connector according to claim 1 or 2 wherein the notches of the female socket are grooves or portions of circular grooves.

5. Connector according to claim 1 wherein the male socket has its adaptation tip designed to receive a male Luer by fitting.

6. Connector according to claim 1 or 5 wherein the female socket has its adaptation tip designed internally with a male Luer able to be fit into a female Luer.

7. Connector according to claim 1 wherein at least one of the adaptation tips is designed to be connected to a cylindrical tube.

8. A connector according to claim 1 or 2 comprising means for connection to a syringe.

9. A connector according to claim 1 or 2 comprising means for connection to a tube.

10. A connector according to claim 1 or 2 comprising means for connection to a needle.

11. A connector according to claim 1 or 2 comprising means for connection to a catheter hub.

12. Medical equipment comprising a connector with a connection tip including a male socket, said connector automatically locking for connecting the Luer cones of two pieces of equipment for medical use, said connector comprising a tubular male socket having an adaptation tip at one end-piece and a tip to be fitted of external conical shape for connection with a tubular female socket having an adaptation tip at one end-piece and a reception tip of internal conical shape able to receive said fitting tip of the male connection with a lateral seal, the male socket being provided with external lateral lugs, the female socket being provided with a set of external notches and the connector comprising a locking collar to be mounted on the two sockets, wherein said collar has lateral ports able to be crossed by said external lateral lugs of the male socket for blocking the collar axially and in rotation on the male socket, and said collar has a transversally deformable part equipped with internal notches, shaped so that the external notches of the collar can pass over the notches of the female socket when the collar is pushed in a direction towards the socket and held by the notches of the female socket when there is traction in the reverse direction, and the notches of the collar and of the female socket being shaped so as to allow relative rotation of the female socket and the collar, said collar comprising zones such that a radial thrust on these zones causes deformation of the collar thus separating the notches of the collar from the notches of the female socket in order to allow separation of the collar and the female socket.

13. Medical equipment comprising a connector with a connection tip including a tubular female socket, said connector automatically locking for connecting the Luer cones of two pieces of equipment for medical use, said tubular female socket having an adaptation tip at one end-piece and a reception tip of internal conical shape able to receive with a lateral seal a fitting tip of a male connection having a tubular male socket with an adaptation tip at one end-piece and a tip to be fitted of external conical shape, the male socket being provided with external lateral lugs, the female socket being provided with a set of external notches and the connector comprising a locking collar to be mounted on the two sockets, wherein said collar has lateral ports able to be crossed by said external lateral lugs of the male socket for blocking the collar axially and in rotation on the male socket, and said collar has a transversally deformable part equipped with internal notches, shaped so that the external notches of the collar can pass over the notches of the female socket when the collar is pushed in a direction towards the socket and held by the notches of the female socket when there is traction in the reverse direction, and the notches of the collar and of the female socket being shaped so as to allow relative rotation of the female socket and the collar, said collar comprising zones such that a radial thrust on these zones causes deformation of the collar thus separating the notches of the collar from the notches of the female socket in order to allow separation of the collar and the female socket.

14. Medical equipment according to claim 12 or 13 wherein said collar comprises two sets of notches diametrically opposite each other and two zones at 90° relative to the notches able to be pushed radially to deform the collar transversally in order to separate the two series of notches from each other in order to allow separation of the collar and the female socket from the connector.

\* \* \* \* \*